United States Patent [19]

Kawabata et al.

[11] Patent Number: 4,801,713

[45] Date of Patent: Jan. 31, 1989

[54] ORGANIC COMPLEXES OF A CATION OF A HETEROCYCLIC NITROGEN COMPOUND AND AN ANION OF A 2,5-DISUBSTITUTED-7,7,8,8-TETRACYANOQUINODIETHMANE

[75] Inventors: Takeo Kawabata, Hirakata; Akira Taisha, Ibaraki, both of Japan

[73] Assignee: Nippon Gohsei Kagaku Kogyo Kabushiki Kaisha, Osaka, Japan

[21] Appl. No.: 147,408

[22] Filed: Jan. 26, 1988

[30] Foreign Application Priority Data

Jan. 27, 1987 [JP] Japan .................. 62-16357

[51] Int. Cl.[4] .................. C07D 217/10; C07D 213/89; C07D 215/58; C07D 233/56
[52] U.S. Cl. ..................... 546/151; 546/181; 546/182; 546/347; 548/335
[58] Field of Search ............... 546/151, 181, 182, 347; 548/335

[56] References Cited

U.S. PATENT DOCUMENTS

| | | | |
|---|---|---|---|
| 2,979,863 | 4/1961 | Bauwin et al. | 546/151 |
| 3,201,399 | 8/1965 | Webster | 546/347 |
| 3,558,671 | 1/1971 | Martin | 546/182 |

Primary Examiner—Glennon H. Hollrah
Assistant Examiner—James H. Turnipseed

Attorney, Agent, or Firm—Armstrong, Nikaido, Marmelstein & Kubovcik

[57] ABSTRACT

Novel, highly electroconductive organic complexes are disclosed which have the general formula $$D^+ \cdot A^-$$

wherein the constituent $D^+$ is an N-alkyl-onium cation ($D^+$) derived from a nitrogen-containing heterocyclic compound (D) selected from the group consisting of pyridines, quinolines, isoquinolines and imidazoles and the constituent $A^-$ is the anion radical corresponding to a 2,5-disubstituted-7,7,8,8-tetracyanoquinodimethane (A) of the general formula

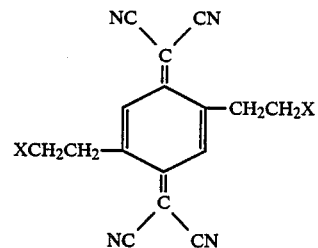

wherein X is —COOR (R being an alkyl group containing 1–10 carbon atoms) or —CN.

2 Claims, No Drawings

ORGANIC COMPLEXES OF A CATION OF A HETEROCYCLIC NITROGEN COMPOUND AND AN ANION OF A 2,5-DISUBSTITUTED-7,7,8,8-TETRACYANOQUINODIETHMANE

BACKGROUND OF THE INVENTION

This invention relates to a novel organic complex composed of a certain derivative of 7,7,8,8-tetracyanoquinodimethane (hereinafter referred to as TCNQ) as the acceptor and an N-alkyl nitrogen-containing heterocyclic compound as the donor.

Electroconductive organic compounds are characterized in that they are light in weight, show anisotropy, can be processed or shaped with ease and can undergo chemical modification. Therefore, they are currently attracting much attention.

Typical of such electroconductive organic compounds are TCNQ complexes composed of nitrogen-containing heterocyclic compounds on one hand and TCNQ on the other. Among the relevant references, there may be mentioned "Synthesis and Application of Organic Semiconductor Materials", published by K.K. C.M.C., 1981, and "Gendai Kagaku (Modern Chemistry)", published by K. K. Tokyo Kagaku Dojin, No. 141, pages 12–19, 1982.

A Japanese patent application laid open under Kokai No. 204173/86 discloses the use of particular 7-membered ring compounds as the nitrogen-containing heterocyclic compound.

However, the above-mentioned TCNQ complexes are insufficient in electroconductivity although they are electroconductive. They melt at relatively high temperatures, hence processing or shaping thereof is subject to restriction. For these and other drawbacks, it is highly desirable to develop electroconductive organic compounds lower in melting point.

Under these circumstances, the present invention has been completed as a result of searching for organic complexes higher in electroconductivity and easier to process and mold as compared with the prior art TCNQ complexes.

SUMMARY OF THE INVENTION

The invention thus provides novel organic complexes of the general formula $$D^+ \cdot A^-$$

wherein the constituent $D^+$ is an N-alkylonium cation derived from a nitrogen-containing heterocyclic compound (D) selected from the group consisting of pyridines, quinolines, isoquinolines and imidazoles and the constituent $A^-$ is an anion radical derived from a 2,5-disubstituted-7,7,8,8-tetracyanoquinodimethane (A) of the general formula

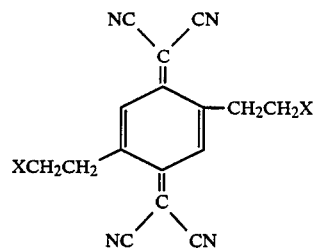

wherein X is —COOR (R being an alkyl group containing 1–10 carbon atoms) or —CN.

DETAILED DESCRIPTION OF THE INVENTION

Compound (A)

The 2,5-disubstituted-7,7,8,8-tetracyanoquinodimethane (A), which is defined by the above formula, is a novel compound not yet described in the literature, and has the skeleton of TCNQ. For said compound (A), Japanese Patent Applications Nos. 166081/85 (Kokai No. 26260/87) and 256255/86 are pending In the above compound (A), X is —COOR or —CN. The group R in said —COOR is an alkyl group and examples of said alkyl group are alkyl groups containing 1–10 carbon atoms, such as methyl, ethyl, propyl, butyl, amyl, hexyl, octyl, decyl and cyclohexyl. Industrially, the use of a lower alkyl group containing about 1–4 carbon atoms is practical The two X groups in the above formula may be different but should preferably be the same from the easy production viewpoint.

The above compound (A), when the two X's are each a —COOCH₃ group, for instance, shows a melting point of 168° C. and is fairly soluble in methanol and other general-use solvents For comparison, TCNQ has a melting point of about 294°–296° C. and is soluble only in several solvents such as acetonitrile, dioxane and dimethylformamide. TCNQ is insoluble in most of other organic solvents.

The above compound (A) can be produced by oxidizing a 2,5-disubstituted-1,4-bis(dicyanomethylene)cyclohexane of the general formula

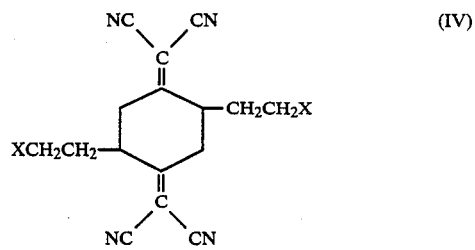

wherein X is as defined above.

The oxidation reaction is carried out in an inert gas atmosphere and generally in a medium such as acetonitrile, using N-bromosuccinimide or bromine as the oxidizing agent. A base such as pyridine is caused to exist in the reaction system.

For said reaction, a reaction temperature of 0° C. to 80° C. and a reaction period of about 0.1–8 hours are sufficient.

Generally, N-bromosuccinimide or bromine is used in an amount of 1–5 moles per mole of the compound (IV).

After completion of the reaction, water is added to the reaction system as necessary. The resultant precipitate is collected and purified in the conventional manner.

The compound (A) in which X is —COOR can also be produced by oxidizing a 2,5-bis(dicyanomethylene)-cyclohexane-1,4-ylene-(3-propionic acid) (IVa), namely the free acid form of compound (IV), and esterifying the resulting 2,5-bis(carboxyethyl)-7,7,8,8-tetracyanoquinodimethane. The esterification is carried out by a per se known method, for example by converting the oxidation product to the corresponding acid chloride by treatment with thionyl chloride, for instance, and then reacting said acid chloride with an alcohol. The esterification reaction may be effected simultaneously during the oxidation reaction by carrying out the oxidation reaction in the presence of an alcohol.

The compound (IV) or (IVa), which is the starting material for the production of the compound (A) in which X is —COOR, can be prepared, for example, by the method described in Japanese Patent Application No. 166081/85 (Kokai No. 26260/87).

Thus, a dialkyl succinylsuccinate of the general formula

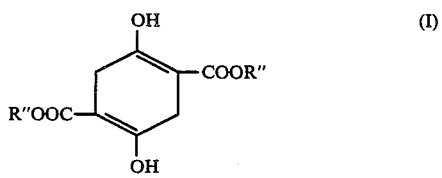

wherein R″ is an alkyl group, is reacted with acrylic acid or an alkyl acrylate of the general formula

CH$_2$=CHCOOR‴ wherein R‴ is a hydrogen atom or an alkyl group, to give a cyclohexane-2,5-dione derivative of the general formula

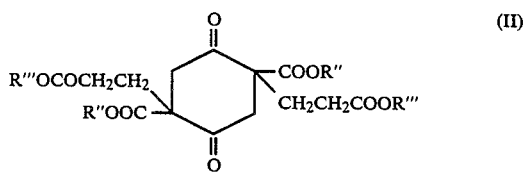

The reaction is generally carried out in an organic solvent in the presence of a metal alcoholate catalyst.

The above cyclohexane-2,5-dione derivative (II) is then heated in an aqueous medium in the presence of a strong acid such as hydrochloric acid, sulfuric acid, p-toluenesulfonic acid or a strong acid form ion exchange resin, to give cyclohexane-2,5-dione-1,4-ylene-(3-propionic acid) of the formula

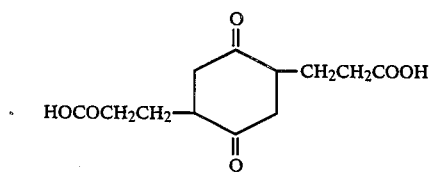

Esterification of this compound (IIIa) gives a cyclohexane-2,5-dione-1,4-ylene-(3-propionic acid alkyl ester) (IIIb), which is one example of the compound of the formula

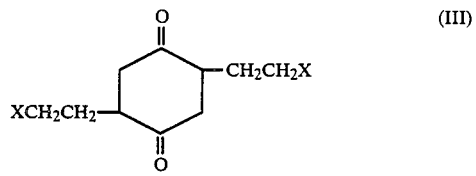

wherein X is as defined above

The subsequent reaction of the compound (IIIb) with malononitrile gives the corresponding 2,5-bis-(dicyanomethylene)cyclohexane-1,4-ylene-(3-propionic acid alkyl ester) (IVb), which is one example of the compound (IV).

Alternatively, the compound (IVb) can also be produced by reacting the above compound (IIIa) first with malononitrile and then esterifying the resulting 2,5-bis(-dicyanomethylene)cyclohexane-1,4-ylene-(3-propionic acid) (IVa)

Furthermore, the compound (IV) or (IVa), which is the starting material for the compound (A), can also be produced by the method described in Japanese Patent Application No. 256255/86.

Thus, cyclohexane-1,4-dione is enaminated with pyrrolidine and the resulting 1,4-dipyrrolidinocyclohexane-1,3-diene is then reacted with acrylic acid, an acrylic ester or acrylonitrile to give the compound (IIIa) or (III).

These reactions are carried out as follows:

The enamine formation reaction with pyrrolidine in the first step converts cyclohexane-1,4-dione to 1,4-dipyrrolidinocyclohexane-1,3-diene.

Benzene, toluene or xylene, for instance, is used as a solvent.

The reaction temperature is preferably a refluxing temperature. The byproduct water formed during the reaction is continuously removed from the reaction system for allowing the reaction to proceed. The use of a catalyst is not essential but an acid such as p-toluenesulfonic acid can be used.

advantageouly, the reaction system is maintained under a nitrogen atmosphere so that the oxidation of the product enamine can be inhibited.

The quantity of pyrrolidine is selected within the range of 2–4 moles per mole of cyclohexane-1,4-dione.

A period of 1–3 hours is suitable as the reaction time.

After removal of the solvent and residual pyrrolidine from the first step reaction mixture, the second step reaction with the unsaturated compound (acrylic acid, acrylate ester or acrylonitrile) is carried out.

Usable solvents are dioxane, dimethylformamide, ethanol, methanol and acetonitrile, among others.

The unsaturated compound is used in an amount of 2–4 moles per mole of cyclohexane-1,4-dione The reaction is conducted under reflux for about 3–24 hours. Then, after addition of water in an amount of about 2 molar equivalents relative to cyclohexane-1,4-dione, hydrolysis is conducted under reflux for about 1–2 hours, whereby the compound (IIIa) or (III) is obtained.

The method of converting the compound (IIIa) or (III) to the compound (IV) is the same as mentioned hereinbefore.

N-Alkyl-onium cation (D+)

The nitrogen-containing heterocyclic compound (D) is selected from the group consisting of pyridines, quinolines, isoquinolines and imidazoles.

The reaction of this nitrogen-containing heterocyclic compound (D) with an alkyl iodide or bromide gives the corresponding N-alkyl-onium cation (D+), namely an N-alkylpyridinium cation, N-alkylquinolinium cation, N-alkylisoquinolinium cation or N-alkylimidazolium cation, in the halide state. Such N-alkylonium cations are represented by the following skeletal formulas:

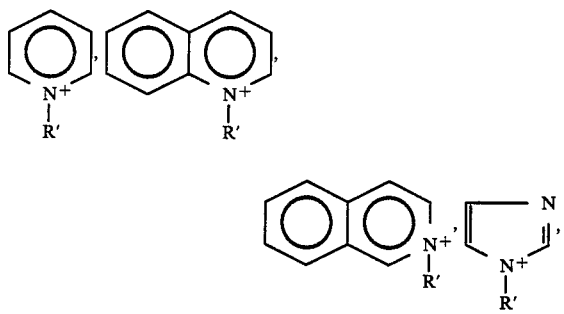

In the above formulas, R' is an alkyl group containing about 1-10 carbon atoms, such as a methyl, ethyl, n-propyl, isopropyl, n-butyl, isobutyl, secbutyl, amyl, hexyl or octyl group. Particularly preferred as the group R' is an alkyl group containing 1-4 carbon atoms.

Organic complex

The organic complex according to the invention is composed of the N-alkyl-onium cation (D+) corresponding to the above-mentioned nitrogen-containing heterocyclic compound (D) and the anion radical (A⁻) corresponding to the above-mentioned compound (A).

This complex can suitably be produced by the following methods:

(i) A warmed solution of an N-alkyl-onium iodide or bromide in a solvent is mixed with a warmed solution of the compound (A) in a solvent and, after cooling, the resulting crystals are collected, washed as necessary, and dried. The N-alkyl-onium iodide or bromide is used in an amount selected within the range of about 0.5-5 moles per mole of the compound (A).

(ii) A warmed solution of an N-alkyl-onium iodide or bromide in a solvent is mixed with a warmed solution of the lithium complex of compound (A) in a solvent and, after cooling, the resulting crystals are collected, washed as necessary, and dried The N-alkyl-onium iodide or bromide is used in an amount selected within the range of about 0.5-5 moles per mole of the lithium complex of compound (A).

Usable as the solvent for reaction and/or washing in the above-mentioned process (i) or (ii) are organic solvents, such as alcohols (methanol, ethanol, n-propanol, isopropanol, etc.), ketones (acetone, methyl ethyl ketone, etc.), nitriles (acetonitrile, etc.), esters (methyl acetate, ethyl acetate, etc.), ethers (dimethyl ether, tetrahydrofuran, etc.), hydrocarbons (hexane, etc.) and cellosolve. Such organic solvents are used either alone or in combination of two or more. Whereas the solvents for TCNQ are limited, the compound (A) is soluble in solvents in general use and this fact broadens the range of solvent selection therefor.

In spite of the fact that its constituents are all organic compounds, the thus-formed complex is highly electroconductive. Therefore, said complex is useful as or in manufacturing an electroconductive paint, electroconductive ink, electroconductive plastic material, electroconductive rubber, high-function electroconductive molecular membrane, electrode, liquid crystal display tube, solar cell, high-density memory, nonlinear optical material, biological element, solid electrolyte and condenser, among others.

Thus the reaction of the 2,5-disubstituted-7,7,8,8-tetracyanoquinodimethane or its lithium salt with the N-alkyl-onium iodide or bromide gives the complex D+.A⁻ whose constituents are the N-alkyl-onium ion (D+) and the anion radical (A⁻) of (A). This complex is a complex of the charge transfer type and shows good electroconductivity.

The novel organic complex according to the invention has a higher electroconductivity than the prior art TCNQ complexes and therefore is suited as an electroconductive material Furthermore, it has a low melting point and therefore is advantageous with respect to processability Accordingly, various applications that cannot be expected of the convettional TCNQ complexes can be expected of the organic complex according to the invention.

EXAMPLES

The following examples are further illustrative of the present invention.

Production of compound (A)

Compound (A-1)

A mixture of 128.13 g (0.5 mole) of diethyl succinylsuccinate (I), 112.4 g (1.0 mole) of methyl acrylate, 2.18 g (0.04 mole) of sodium methylate and 700 ml of methanol were refluxed in an argon atmosphere for 15 hours. Then, the methanol was distilled off under reduced pressure, a small quantity of wtter with benzene added thereto was added to the residue and, after phase separation, the benzene layer was dried and then distilled under reduced pressure to give 181.97 g of the cyclohexane-2,5-dione derivative (II) as a yellowish brown oil.

A mixture of 177.55 g (0.414 mole) of the cyclohexane-2,5-dione derivative (II) obtained as described above, 300 ml of water and 10 g of concentrated sulfuric acid was refluxed Since the boiling point lowered with the progress of the reaction, the methanol and ethanol were distilled off from time to time. After 120 hours of refluxing, the methanol and ethanol then remaining in the reaction mixture were distilled off and the residual reaction mixture was cooled.

The resultant crystalline precipitate was collected by filtration, whereby 29.98 g of a product melting at 190° C. was obtained. Recrystallization from water gave cyclohexane-2,5-dione-1,4-ylene-(3-propionic acid) (IIIa) melting at 192°-194° C.

A solution f 12.8 g (50 millimoles) of cyclohexane-2,5-dione-1,4-ylene-(3-propionic acid) (IIIa) obtained as described above in 300 ml of water was neutralized with an equivalent quantity of sodium hydrogen carbonate, then 6.6 g (100 millimoles) of malononitrile and 1.0 g of β-alanine were added, and the mixture was heated on a water bath for 2 hours, then cooled and made acidic with diluted hydrochloric acid. The resultant crystalline precipitate was collected by filtration, washed and dried to give 8.6 g of 2,5-bis(dicyanomethylene)cyclohexane-1,4-ylene-(3-propionic acid) (IVa).

2,5-Bis(dicyanomethylene)cyclohexane-1,4-ylene-(3-propionic acid) (IVa) (8.6 g) obtained as described above was dissolved in methanol, then 31.0 g of thionyl chloride was added at 10° C., and the mixture was stirred for 2 hours. The resultant crystals were collected by filtration, washed and dried to give 8.3 g of 2,5-bis(dicyanomethylene)cyclohexane-1,4-ylene-(3-propionic acid methyl ester) (IV).

2,5-Bis(dicyanomethylene)cyclohexane-1,4-ylene-(3-propionic acid methyl ester) (IV) (5.7 g) obtained as described above was suspended in 500 ml of acetonitrile and, after argon substitution, 6.0 g of N-bromosuccinimide was added. The resultant mixture was stirred for 1 hour. After cooling, 9.0 g of pyridine was added and the mixture was stirred while the temperature of the system was maintained at 10° C. or below. Then, 300 ml of water was added, and the resultant precipitate was collected by filtration, washed with water and dried to give 5.1 g of the desired compound The yield was 90% based on 2,5-bis(dicyanomethylene)cyclohexane-1,4-ylene-(3-propionic acid methyl ester) (IV).

This compound had the following characteristics and was identified as 2,5-bis[(methoxycarbonyl)ethyl]-7,7,8,8-tetracyanoquinodimethane (A-1) of the formula:

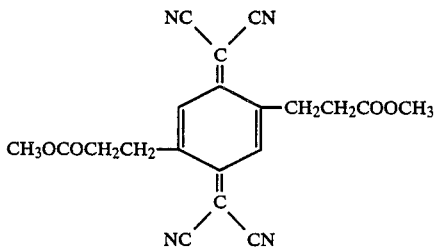

Melting point: 167°-168° C.

IR, $\nu$cm$^{-1}$ (KBr): 3050, 2960, 2215, 1740, 1550, 1515, 1200, 1175, 915, 900.

NMR, $\delta$ ppm (CDCl$_3$): 7.33 (2H, s), 3.70 (6H, s), 3.33 (4H, t), 2.73 (4H, t).

Mass spectrum, m/e: 376, 345, 344, 317, 303, 259, 258 (B), 257.

Compound (A-2)

Oxidation of 2,5-bis(dicyanomethylene)cyclohexane-1,4-ylene-(3-propionic acid ethyl ester) (IV) gave 2,5-bis[(ethoxycarbonyl)ethyl]-7,7,8,8-tetracyanoquinodimethane (A-2).

Compound (A-3)

A mixture of 11.2 g (0.1 mole) of cyclohexane-1,4-dione, 21.3 g (0.3 mole) of pyrrolidine and 45 ml of toluene was refluxed for 3 hours in a nitrogen gas stream with byproduct water being removed.

The toluene and unreacted pyrrolidine were removed, ml of dioxane and 15.9 g (0.3 mole) of acrylonitrile were added, and the mixture was refluxed for 12 hours Thereafter, 5 ml of water was added and the refluxing was continued for another hour.

After completion of the reaction, the unreacted acrylonitrile and dioxane were removed from the reaction mixture, 300 ml of water was added, and the resultant mixture was extracted with chloroform.

The chloroform layer was washed with 10% hydrochloric acid and then with water, and dried over sodium sulfate. The chloroform was distilled off from the extract. The crystalline residue (10.9 g) was recrystallized from methanol to give a colorless crystalline product melting at 147.8° C.

This crystalline product was identified as the compound (III), namely 2,5-bis(2-cyanoethyl)cyclohexane-1,4-dione, as a result of analysis of its NMR spectrum, mass spectrum and IR spectrum.

A mixture of 873 mg of the compound (III) obtained in the above manner, 3.4 g of water, 5.0 g of methanol and 9.9 mg of $\beta$-alanine was heated When the reaction vessel inside temperature reached 45° C., a solution of 536 mg of malononitrile in 1.6 g of methanol was added all at once, and the reaction was conducted at 45°-50° C. for 1.5 hours.

After completion of the reaction, the reaction mixture was cooled to room temperature, and the crystals were collected by filtration, washed with water and then with methanol, and dried under reduced pressure to give 1.24 g of a crystalline product.

This crystalline product had the characteristic values given below and was identified as the compound (IV), namely, 2,5-bis(2-cyanoethyl)cyclohexane-1,4-bis(dicyanomethylene). The yield was 98.6% based on the compound (III).

Melting point: 216°-220° C.

IR (KBr), $\nu$ (cm$^{-1}$): 3930, 2240, 1720, 1610, 1435

NMR (DMSO-d$_6$), $\delta$ (ppm): 1.6-3.5 (m, 14H)

Mass spectrum, M+: 314

A mixture of 0.94 g of the compound (IV) obtained in the above manner and 31 g of acetonitrile was heated. When the inside temperature reached 70° C., a solution of 0.95 g of pyridine in acetonitrile and a solution of 0.98 g of bromine in acetonitrile were added at the same time, and the reaction was conducted at 70°-75° C. for 15 minutes.

After completion of the reaction, the reaction mixture was cooled to room temperature, and the crystals were collected by filtration, washed with water, methanol and acetone in that order, and dried to give 0.58 g of a crystalline product.

The crystalline product obtained had the characteristic values given below and was identified as the compound (A-3), namely 2,5-bis(2-cyanoethyl)-7,7,8,8-tetracyanoquinodimethane. The yield was a 62.5% based on the compound (IV).

Melting point: 210°-220° C.

IR (KBr), $\nu$ (cm$^{-1}$): 2210, 1555, 1525, 1470, 1420, 890, 460.

N-Alkyl-onium iodide (D+I−)

The following N-alkyl-onium iodides (D+I−) were obtained by reacting pyridine, quinoline, isoquinoline or 2-phenyl imidazole with an equimolar amount of methyl iodide, ethyl iodide, n-propyl iodide, isopropyl iodide or n-butyl iodide:

D-1+I−: N-Methylpyridinium iodide,
D-2+I−: N-n-Butylpyridinium iodide,
D-3+I−: N-Ethylquinolinium iodide,
D-4+I−: N-Isopropylquinolinium iodide,
D-5+I−: N-Ethylisoquinolinium iodide,
D-6+I−: N-n-Propylisoquinolinium iodide,
D-7+I−: N-n-Butylisoquinolinium iodide,
D-8+I−: 3-n-Butyl-1-methylimidazolium iodide, and D-9+I−: 3-n-Butyl-2-phenylimidazolium iodide.

EXAMPLES 1-24

Organic complexes were produced by either of the methods (i) and (ii) mentioned below using the above-mentioned compounds (A) and various N-alkyl-oniuim iodides (D+I−) mentioned above (i) A warmed solution of 7.3 millimoles (e.g. 2.75 g in the case of A-1) of compound (A) in acetonitrile was mixed with a warmed solution of 18.3 millimoles of N-alkyl-onium iodide (D+I−) in acetonitrile, and the mixture was allowed to cool to and stand at room temperature. The resultant crystalline precipitate was collected by filtration, washed with acetonitrile and dried under vacuum to give a complex.

(ii) A warmed solution of 6.0 millimoles (2.30 g in the case of A-1) of the lithium complex of compound (A) in ethanol was mixed with a warmed solution of 6.0 millimoles of N-alkyl-onium iodide (D+I−) in acetonitrile, and the mixture was allowed to cool to and stand at room temperature. The resultant crystalline precipitate was collected by filtration, washed with ethanol and dried under vacuum to give a complex.

The characteristics of the complexes thus obtained are shown in Table 1.

Furthermore, the resistivity and elemental analysis values of the complexes obtained are shown in Table 2. For comparison, the resistivities of some TCNQ complexes obtained by the conventional method are also shown in Note 2 to Table 2.

The resistivity values were determined by pressure molding of each complex by the conventional method, resistance measurement by the two-terminal method and calculation using the equation:

*Resistivity* ($\Omega \cdot cm$) = *resistance* ($\Omega$) × *electrode contact area* ($cm^2$)/*specimen thickness* ($cm$).

TABLE 1

| Example | Reactants | | Product complex | Method of production | Yield (%) | Appearance | Melting point (°C.) |
|---|---|---|---|---|---|---|---|
| 1 | D-1+I− | A-1 | D-1+.A-1 | (i) | 23.4 | Black green needles | 165.5–167 |
| 2 | D-1+I− | Li+A-1 | D-1+.A-1 | (ii) | 41.4 | Black green needles | 168–169 |
| 3 | D-2+I− | A-1 | D-2+.A-1 | (i) | 64.3 | Dark green purple crystals | 138–139 |
| 4 | D-2+I− | Li+A-1 | D-2+.A-1 | (ii) | 60.5 | Black green purple crystals | 137–139 |
| 5 | D-3+I− | A-1 | D-3+.A-1 | (i) | 39.5 | Blue green needles | 163.5–165 |
| 6 | D-3+I− | Li+A-1 | D-3+.A-1 | (ii) | 53.6 | Blue green needles | 158–160 |
| 7 | D-4+I− | A-1 | D-4+.A-1 | (i) | 22.0 | Black green blue needles | 159–160 |
| 8 | D-4+I− | Li+A-1 | D-4+.A-1 | (ii) | 41.8 | Black green blue needles | 157–165 |
| 9 | D-5+I− | A-1 | D-5+.A-1 | (i) | 56.0 | Black purple needles | 185–186.5 |
| 10 | D-5+I− | Li+A-1 | D-5+.A-1 | (ii) | 84.2 | Black purple needles | 183–185 |
| 11 | D-6+I− | A-1 | D-6+.A-1 | (i) | 58.5 | Black purple needles | 178–180 |
| 12 | D-6+I− | Li+A-1 | D-6+.A-1 | (ii) | 82.6 | Black purple needles | 179–180 |
| 13 | D-7+I− | A-1 | D-7+.A-1 | (i) | 89.0 | Black purple needles | 164–166 |
| 14 | D-7+I− | Li+A-1 | D-7+.A-1 | (ii) | 72.0 | Black purple needles | 164–165.5 |
| 15 | D-1+I− | A-2 | D-1+.A-2 | (i) | 33.9 | Deep green crystals | 142–145 |
| 16 | D-1+I− | Li+A-2 | D-1+.A-2 | (ii) | 57.8 | Deep green crystals | 144–145 |
| 17 | D-5+I− | A-2 | D-5+.A-2 | (i) | 40.4 | Deep green crystals | 130–133 |
| 18 | D-5+I− | Li+A-2 | D-5+.A-2 | (ii) | 61.3 | Deep green crystals | 131–133 |
| 19 | D-7+I− | A-2 | D-7+.A-2 | (i) | 38.2 | Deep green crsytals | 102–104 |
| 20 | D-7+I− | Li+A-2 | D-7+.A-2 | (ii) | 47.2 | Deep green crystals | 102–104 |
| 21 | D-1+I− | A-3 | D-1+.A-3 | (i) | 72.7 | Black purple needles | 190–193 |
| 22 | D-1+I− | Li+A-3 | D-1+.A-3 | (ii) | 92.7 | Deep purple needles | 188–192 |
| 23 | D-8+I− | A-3 | D-8+.A-3 | (i) | 46.9 | Deep green crystals | 125–129 |
| 24 | D-9+I− | A-3 | D-9+.A-3 | (i) | 43.2 | Deep green crystals | 174–177 |

TABLE 2

| Complex | Resistivity ($\Omega \cdot cm$) | Chemical formula | Elemental analysis | | |
|---|---|---|---|---|---|
| | | | C (%) | H (%) | N (%) |
| D-1+.A-1 | $8.4 \times 10^3$ | $C_{26}H_{24}N_5O_4$ | 66.4 | 5.14 | 14.9 |
| | | | 66.1 | 5.61 | 15.3 |
| D-2+.A-1 | $2.8 \times 10^4$ | $C_{29}H_{30}N_5O_4$ | 68.0 | 5.90 | 13.7 |
| | | | 68.4 | 6.26 | 14.1 |
| D-3+.A-1 | $2.5 \times 10^4$ | $C_{31}H_{28}N_5O_4$ | 69.7 | 5.28 | 13.1 |
| | | | 69.4 | 5.46 | 13.3 |
| D-4+.A-1 | $2.7 \times 10^3$ | $C_{32}H_{30}N_5O_4$ | 70.1 | 5.51 | 12.8 |
| | | | 70.6 | 5.95 | 13.1 |
| D-5+.A-1 | $6.2 \times 10^3$ | $C_{31}H_{28}N_5O_4$ | 69.7 | 5.28 | 13.1 |
| | | | 70.2 | 5.64 | 12.8 |
| D-6+.A-1 | $3.9 \times 10^4$ | $C_{32}H_{30}N_5O_4$ | 70.1 | 5.51 | 12.8 |
| | | | 69.7 | 5.80 | 12.5 |
| D-7+.A-1 | $2.7 \times 10^4$ | $C_{33}H_{32}N_5O_4$ | 70.5 | 5.73 | 12.5 |
| | | | 70.7 | 6.13 | 12.2 |
| D-1+.A-2 | $4.2 \times 10^3$ | $C_{28}H_{28}N_5O_4$ | 67.5 | 5.66 | 14.0 |
| | | | 67.3 | 5.41 | 14.2 |
| D-5+.A-2 | $4.5 \times 10^4$ | $C_{33}H_{32}N_5O_4$ | 70.4 | 5.73 | 12.4 |
| | | | 70.6 | 5.90 | 12.4 |
| D-7+.A-2 | $2.4 \times 10^4$ | $C_{35}H_{36}N_5O_4$ | 71.2 | 6.14 | 11.9 |
| | | | 71.6 | 6.49 | 12.1 |
| D-1+.A-3 | $4.9 \times 10^3$ | $C_{24}H_{18}N_7$ | 71.3 | 4.48 | 24.2 |
| | | | 71.3 | 4.35 | 24.5 |
| D-8+.A-3 | $1.5 \times 10^5$ | $C_{26}H_{25}N_8$ | 69.5 | 5.61 | 24.9 |
| | | | 69.5 | 5.48 | 25.0 |
| D-9+.A-3 | $4.9 \times 10^5$ | $C_{31}H_{27}N_8$ | 72.8 | 5.32 | 21.9 |
| | | | 72.7 | 5.50 | 21.8 |

Note 1: In the elemental analysis columns, the upper row values are theoretical ones while the lower row values are found ones.
Note 2: The resistivity of D-1+.TCNQ is $6.3 \times 10^4$. The resistivity of D-7+.TCNQ is $8.2 \times 10^5$.

What is claimed is:
1. A novel organic complex of the general formula

$$D^+ . A^{\overline{\cdot}}$$

wherein the constituent D+ is an N-alkyl-onium cation (D+) derived from a nitrogen-containing heterocyclic compound (D) selected from the group consisting of pyridines, quinolines, isoquinolines and imidazoles and the constituent A− is the anion radical corresponding to a 2,5-disubstituted-7,7,8,8-tetracyanoquinodimethane (A) of the general formula

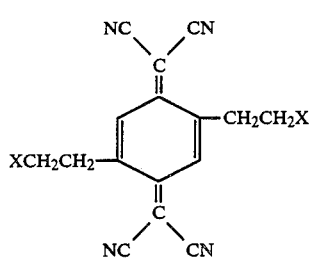
wherein X is —COOR (R being an alkyl group containing 1-10 carbon atoms) or —CN.
2. An organic complex as claimed in claim 1, wherein X is —COOR in which R is a lower alkyl group containing 1-4 carbon atoms.
* * * * *